US009850750B1

(12) United States Patent
DiFoggio

(10) Patent No.: US 9,850,750 B1
(45) Date of Patent: Dec. 26, 2017

(54) SONOLUMINESCENCE SPECTROSCOPY FOR REAL-TIME DOWNHOLE FLUID ANALYSIS

(71) Applicant: BAKER HUGHES INCORPORATED, Houston, TX (US)

(72) Inventor: Rocco DiFoggio, Houston, TX (US)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 6 days.

(21) Appl. No.: 15/184,810

(22) Filed: Jun. 16, 2016

(51) Int. Cl.
*E21B 47/00* (2012.01)
*E21B 47/12* (2012.01)
*E21B 47/18* (2012.01)
*G01N 29/24* (2006.01)
*G01N 21/954* (2006.01)

(52) U.S. Cl.
CPC ........ *E21B 47/0002* (2013.01); *E21B 47/123* (2013.01); *E21B 47/18* (2013.01); *G01N 29/2418* (2013.01); *G01N 2021/9544* (2013.01); *G01N 2021/9546* (2013.01)

(58) Field of Classification Search
CPC ............. G01N 21/954; G01N 21/9544; G01N 2021/9546; G01N 2021/9548; G01N 33/2823; G01N 29/2418; G02N 2021/9542; G02B 23/24; G02B 23/2407; E21B 47/0002; E21B 47/0003; E21B 47/00; E21B 47/0001; E21B 47/123; E21B 47/18
USPC ...................................................... 356/241.1
See application file for complete search history.

(56) References Cited

U.S. PATENT DOCUMENTS 4,446,395 A 5/1984 Hadjicostis
4,779,201 A * 10/1988 Iizuka ...................... G01V 8/02
  324/338
5,276,656 A * 1/1994 Angehrn ............. E21B 47/0002
  367/86

(Continued)

OTHER PUBLICATIONS

Suslick, Kenneth S. et al., "Sonoluminescence From Non-Aqueous Liquids," Letters to Nature, vol. 330, pp. 553-555 (1987).

(Continued)

*Primary Examiner* — Michael P Lapage
(74) *Attorney, Agent, or Firm* — Mossman, Kumar & Tyler, PC

(57) ABSTRACT

Methods, systems, devices, and products for evaluating a downhole fluid in a borehole intersecting an earth formation. Methods include using ultrasonic irradiation to produce sonoluminescence from cavitation in a volume of the fluid; obtaining spectral information from measurement of the sonoluminescence with a light-responsive device; and estimating a parameter of interest of the fluid from the spectral information. The parameter may be a composition of the fluid or concentration of: i) at least one chemical element in the volume; i) at least one molecular element in the volume. Methods include deconvolving a response spectrum by using one or more separately determined standard spectra, or estimating the parameter of interest using spectral lines represented by the spectral information. Methods may include using an optically transparent ultrasonic transducer to produce the cavitation at the interface of the transducer, with optically transparent ultrasonic transducer between the interface and the light-responsive device.

14 Claims, 7 Drawing Sheets

(56) References Cited

U.S. PATENT DOCUMENTS

| | | | | |
|---|---|---|---|---|
| 6,041,248 | A * | 3/2000 | Wang | G01N 21/4795 |
| | | | | 600/407 |
| 6,176,323 | B1 * | 1/2001 | Weirich | E21B 21/08 |
| | | | | 175/40 |
| 7,906,023 | B2 | 3/2011 | Johnson | |
| 8,882,997 | B2 | 11/2014 | Johnson | |
| 8,921,768 | B2 | 12/2014 | Jones et al. | |
| 2005/0254345 | A1 * | 11/2005 | Ferrell | G01N 21/1702 |
| | | | | 367/131 |
| 2008/0058647 | A1 * | 3/2008 | Kruger | A61B 5/0261 |
| | | | | 600/454 |
| 2009/0169428 | A1 | 7/2009 | Gillespie et al. | |
| 2010/0133447 | A1 * | 6/2010 | Gaitan | B01J 19/008 |
| | | | | 250/432 R |
| 2010/0305499 | A1 * | 12/2010 | Matsiev | A61B 5/145 |
| | | | | 604/67 |
| 2012/0312530 | A1 * | 12/2012 | Pope | E21B 47/102 |
| | | | | 166/250.01 |

OTHER PUBLICATIONS

Suslick, Kenneth S. et al., "Inside a Collapsing Bubble: Sonoluminescence and the Conditions During Cavitation," Annu. Rev. Phys. Chem. 59: 659-83 (2008).

Zeiger, Bradley Weston, "Bubbles and Crystals: Tim-Resolved Sonoluminescence, Sonocrystallization, and Sonofragmentation," Graduate School Thesis (2012).

Merouani, Slimane et al., "Theoretical Estimation of the Temperature and Pressure Within Collapsing Acoustical Bubbles," Ultrasonics Sonochemistry 21, pp. 53-59 (2014).

* cited by examiner

SONOLUMINESCENCE SPECTROSCOPY FOR REAL-TIME DOWNHOLE FLUID ANALYSIS

FIELD OF THE DISCLOSURE

This disclosure generally relates to borehole tools, and in particular to methods and apparatuses for conducting downhole measurements.

BACKGROUND OF THE DISCLOSURE

Drilling wells for various purposes is well-known. Such wells may be drilled for geothermal purposes, to produce hydrocarbons (e.g., oil and gas), to produce water, and so on. Well depth may range from a few thousand feet to 25,000 feet or more. In hydrocarbon wells, downhole tools often incorporate various sensors, instruments and control devices in order to carry out any number of downhole operations. Thus, the tools may include sensors and/or electronics for formation evaluation, fluid analysis, monitoring and controlling the tool itself, and so on. Tools that allow testing of fluid properties using instruments located downhole are known.

SUMMARY OF THE DISCLOSURE

In aspects, the present disclosure is related to methods and apparatuses for estimating at least downhole parameter relating to an earth formation intersected by a borehole, such as, for example, a parameter indicating a property of the formation, the borehole, or the fluid therein.

Methods embodiments may include evaluating a downhole fluid. Methods may include using ultrasonic irradiation to produce sonoluminescence from cavitation in a volume of the fluid; obtaining spectral information from measurement of the sonoluminescence with a light-responsive device; and estimating a parameter of interest of the fluid from the spectral information. The parameter of interest may be a composition of the fluid. The parameter of interest may be the concentration of at least one of: i) at least one chemical element in the volume; i) at least one molecular element in the volume. Methods may include deconvolving a response spectrum represented by the spectral information by using one or more separately determined standard spectra. Methods may include estimating the parameter of interest using spectral lines represented by the spectral information. Methods may include using an optically transparent ultrasonic transducer to produce the cavitation at the interface of the transducer; wherein the optically transparent ultrasonic transducer is disposed between the interface and the light-responsive device. The optically transparent ultrasonic transducer may serve as an optical window for the sonoluminescence to reach the light-responsive device.

Obtaining spectral information may be carried out by collecting the light emissions from at least one cavitation bubble by an optical sensor. The sonoluminescence may include light emissions over a spectrum of wavelengths, and the spectral information is reflective of the spectrum of wavelengths. Methods may include using the parameter of interest to estimate a characteristic of a formation associated with the fluid. The characteristic may be compartmentalization.

Apparatus embodiments may include an ultrasonic irradiation device acoustically coupled with the fluid and configured to produce sonoluminescence from cavitation in a volume of the fluid; a light-responsive device optically coupled with the fluid and configured to obtain spectral information from measurement of the sonoluminescence; and at least one processor configured to estimate a parameter of interest of the fluid from the spectral information. The apparatus may include a conveyance device configured to convey the ultrasonic transducer and the light-responsive device in the borehole. The ultrasonic irradiation device may comprise an optically transparent ultrasonic transducer configured to produce cavitation in the fluid at the interface of the transducer and the fluid; and wherein the optically transparent ultrasonic transducer is disposed between the interface and the light-responsive device.

Examples of some features of the disclosure may be summarized rather broadly herein in order that the detailed description thereof that follows may be better understood and in order that the contributions they represent to the art may be appreciated.

BRIEF DESCRIPTION OF THE DRAWINGS

For a detailed understanding of the present disclosure, reference should be made to the following detailed description of the embodiments, taken in conjunction with the accompanying drawings, in which like elements have been given like numerals, wherein.

DETAILED DESCRIPTION

Figure 1A:
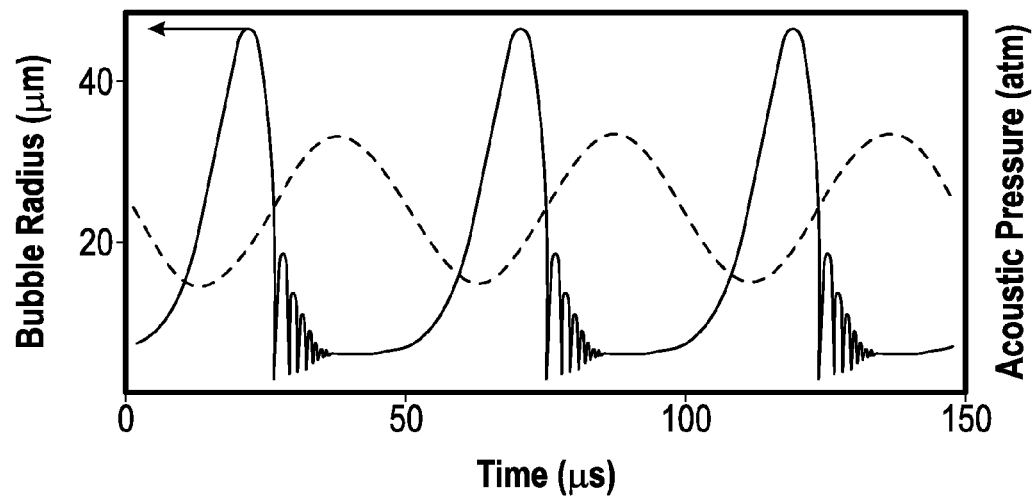
FIGS. 1A-1E illustrate cavitation conditions.

Aspects of the present disclosure relate to apparatus and methods for downhole logging with respect to fluid evaluation, including measurement and interpretation of physical phenomena indicative of parameters of interest of the formation, the borehole, or the downhole fluids therein. Techniques described herein are particularly suited to measurement of values of properties of a downhole fluid through the use of instruments utilizing sonoluminescence phenomena. These values may be used to evaluate and model the formation or the borehole, and for conducting further operations in the formation or the borehole.

As used herein, the term "fluid" and "fluids" refers to one or more gasses, one or more liquids, and mixtures thereof. A "downhole fluid" as used herein includes any gas, liquid, flowable solid and other materials having a fluid property and relating to hydrocarbon recovery. A downhole fluid may be natural or man-made and may be transported downhole or may be recovered from a downhole location. Non-limiting examples of downhole fluids include drilling fluids, return fluids, formation fluids, production fluids containing one or more hydrocarbons, engineered fluids, oils and solvents used in conjunction with downhole tools, water, brine, and combinations thereof. An "engineered fluid" may be used herein to mean a human made fluid formulated for a particular purpose.

Aspects of the present disclosure relate to modeling a volume of an earth formation. The model of the earth formation generated and maintained in aspects of the disclosure may be implemented as a representation of the earth formation stored as information. The information (e.g., data) may be stored on a non-transitory machine-readable medium, transmitted, and rendered (e.g., visually depicted) on a display.

The irradiation of a liquid with sound of sufficient pressure may cause the formation and oscillation of bubbles. Acoustic cavitation may be defined as the growth and rapid collapse of bubbles in a liquid irradiated with high intensity sound, such as, for example, ultrasound. Cavitation may be formed in fluid in an ultrasonic field having a elevated frequency, such as, for example, a frequency of 20 kHz to 2 MHz or higher. The bubbles may be formed from pre-existing impurities and oscillate with the applied sound field. These cavitation bubbles may be driven into highly non-linear oscillations, which may be characterized by low rates of initial volume growth followed by compression and subsequent exponential implosion. Cavitation results in extreme conditions within the bubble, such as, for example, temperatures up to 20,000 K, pressures of several thousand bar, and heating and cooling rates of greater than $10^{12}$ Ks−1.

One product of this cavitation is the emission of light, referred to as sonoluminescence. Although the exact physical mechanism is not settled, it is thought that the light may arise from compressional heating of the medium. Insonication of organic solvents have been shown to result in emission bands and lines from electronically excited molecules and atoms. See K. Suslick and D. Flannigan. Inside a Collapsing Bubble: Sonoluminescence and the Conditions During Cavitation. *Annu. Rev. Phys. Chem.* 2008. 59:659-83; and K. Suslick and E. Flint. Sonoluminescence from non-aqueous liquids. *Nature,* 10 Dec. 1987, Vol. 330:553-55 (collectively, 'Suslick'). The spectral features of this emitted light change over the time that the temperature is dropping from its maximum value back down to ambient temperature. Atomic emission spectra dominate initially at the highest temperatures, whereas molecular vibrational bond emission spectra can become apparent later at lower temperatures.

A single bubble may also be trapped in a standing wave, which also results in conditions extreme enough to cause light emission from excitation of gas molecules in the bubble, referred to as single-bubble sonoluminescence (hereinafter 'SBSL'). In practice, acoustic nucleation of a bubble may be carried out with only around one bar of pressure due to the presence of nucleation sites (e.g., tiny gas bubbles already present in solution, gas pockets in crevices in particulate impurities, etc.). B. Zeiger. Bubbles and crystals: time-resolved sonoluminescence, sonocrystallization, and sonofragmentation. Diss. University of Illinois at Urbana-Champaign, 2013. Beneficially, SBSL pulses may have very stable periods and positions—the frequency of light flashes may be even more stable than the frequency stability of the oscillator producing the sound waves.

Figure 1B:
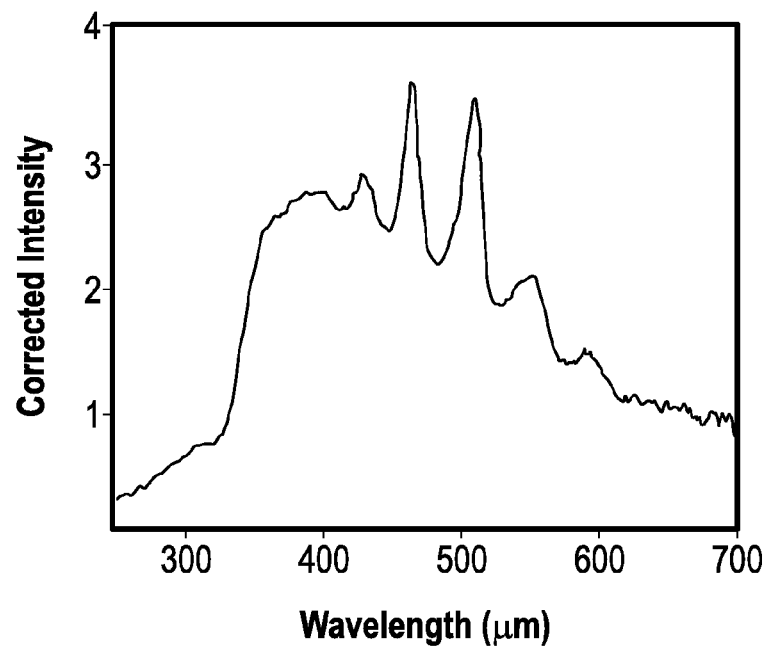
Figure 1C:
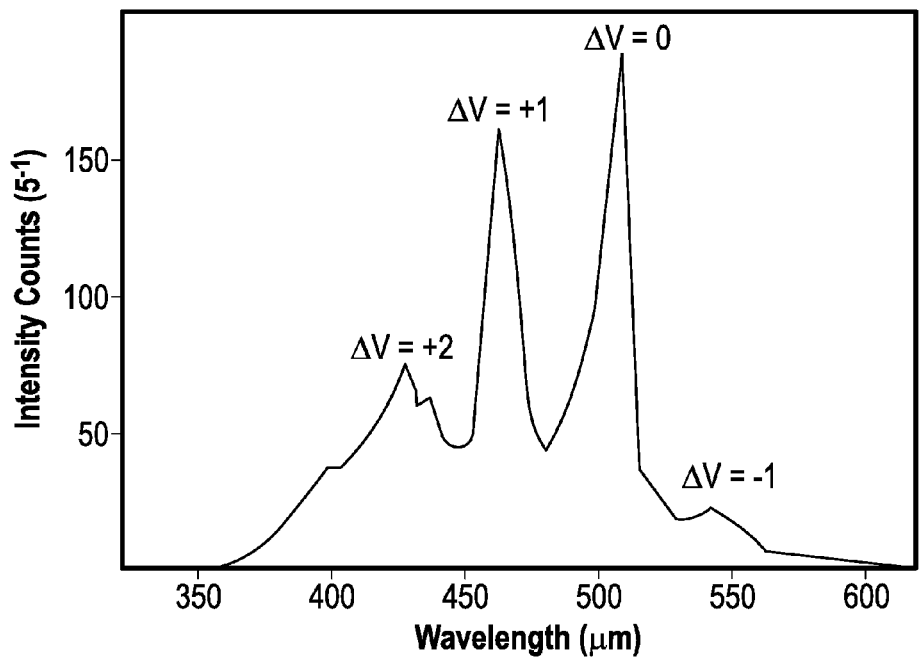
Figure 1D:
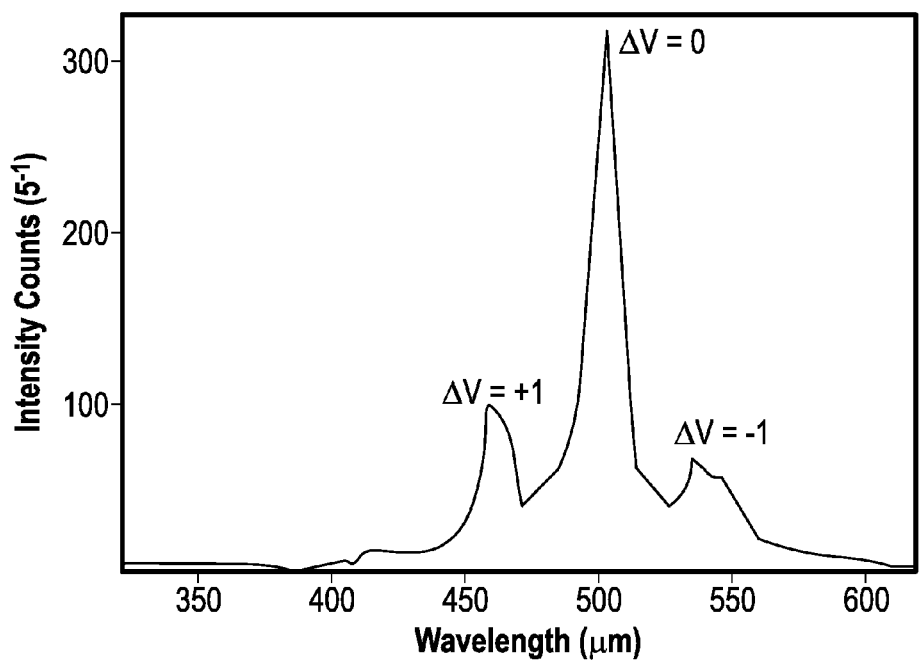
Figure 1E:
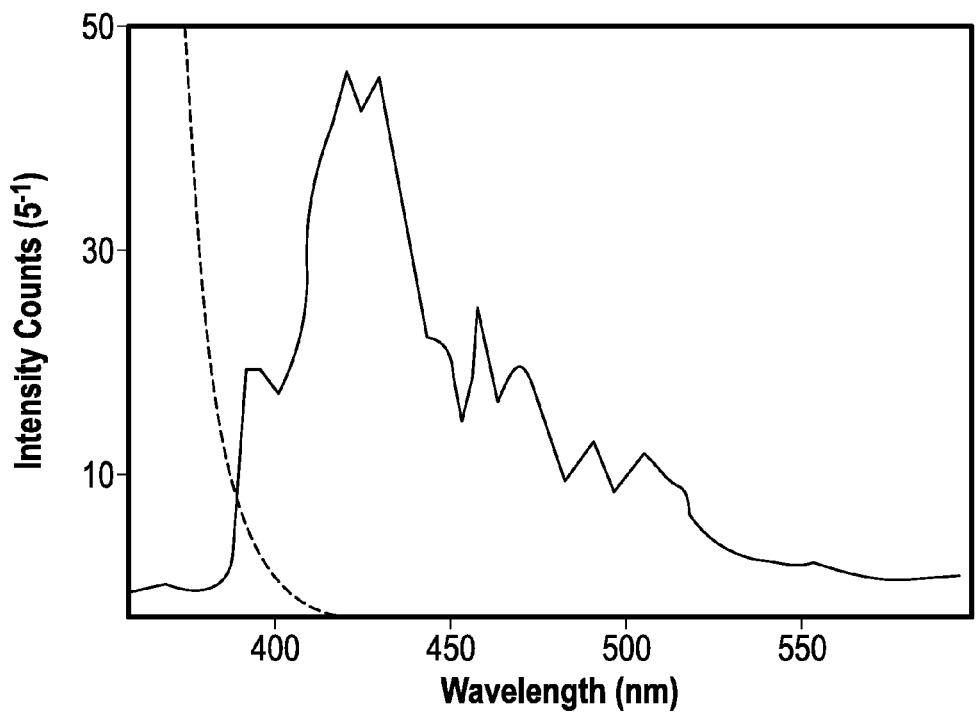

FIGS. 1A-1E illustrate cavitation conditions as described by Suslick. FIG. 1A shows a calculated radial response of a bubble driven by a sinusoidal acoustic field in a medium in cavitation conditions. FIG. 1B shows a multibubble sonoluminescence spectrum generated from the insonication of Argon saturated dodecane at 4 degrees Celsius. FIG. 1C shows a multibubble sonoluminescence spectrum generated from the insonication of dodecane under Argon at −4 degrees Celsius and 0.006 torr. FIG. 1D shows a multibubble sonoluminescence spectrum generated from the insonication of tetrachloroethylene under Argon at −16 degrees Celsius and 1.3 torr. FIG. 1E shows a multibubble sonoluminescence spectrum generated from the insonication of nitroethane under Argon at −19 degrees Celsius and 1.1 torr.

Referring to FIG. 1A, the bubble's initial phase of slow growth begins as the acoustic pressure wave enters rarefaction. A large portion of this phase may be characterized by essentially linear growth. As the acoustic pressure wave enters a compression phase, the bubble motion strongly deviates from linear compression. The bubble's continued expansion at this point may be described as inertial. Bubble growth is quickly arrested at $R_{max}$, i.e., the maximum bubble radius, and begins a rapid (and eventually runaway) collapse. The velocity of late stage collapse may reach several times the speed of sound in gas at ambient temperature and pressure. The bubble rapidly passes through $R_0$ and continues to diminish until $R_{min}$ is achieved, around which time high-energy chemical reactions and light emission occur. The bubble then goes through a series of secondary compressions and expansions of diminishing amplitude at roughly the Minnaert frequency (24, 25) until finally coming to rest again at $R_0$ (K. Suslick and D. Flannigan). Referring to FIGS. 1B and 1C, the sonoluminescence spectrum of dodecane comes from the excited stat $C_2$, and more specifically from the Swan band. Referring to FIG. 1C, the four bands at 435 nm, 465 nm, 510 nm, and 550 nm correspond to Δv or +2, +1, 0, and −1, respectively, of the vibrational manifold. The spectra for mesitylene, 4-heptanone, and n-butylcyanide have lower intensities and changes between relative intensities of vibrational bands. Referring to FIG. 1D, the spectrum for tetrachloroethylene may also be assigned to the $C_2$ Swan band. In contrast, the spectra for nitroethane in FIG. 1E may be attributed to beta band transitions.

As a result, the light emissions from cavitation in the fluid may be analyzed and correlated with properties of the fluid. For example, the sonoluminescence phenomena enables spectroscopic measurement of the fluid. General method embodiments include using an ultrasonic transducer (which may be coin-shaped with opaque metal electrodes covering each face) to produce sonoluminescence from cavitation in a volume of the fluid; obtaining spectral information from measurement of the sonoluminescence with a light-responsive device; and estimating a parameter of interest of the fluid from the spectral information. The parameter of interest may include a composition of the fluid, such as, for example, the concentration of at least one chemical element in the volume.

However, many downhole fluids are non-transparent (e.g., substantially opaque). Crude oil, for instance, is very dark—thus, it is far from optically transparent so sonoluminescent light would likely be largely or completely absorbed if the collapsing bubble were separated from the optical detection device by even a millimeter of crude oil. Therefore, aspects of the present disclosure include using an optically transparent acoustic transducer assembly having optically transparent components to create cavitation bubbles in non-transparent downhole fluids at the interface of the transducer and the fluid. Therefore, the transparent acoustic transducer, with its transparent electrode faces, acts as both the initiator of sonoluminescence and the optical window for passage of light generated by bubble collapse at the window-fluid interface. Sonoluminescence would then be collected using a spectrometer that is located behind the transparent transducer for the purpose of real-time molecular and elemental analysis of the crude oil or other downhole fluid.

In aspects, this disclosure relates to making a downhole measurement. Downhole measurement, as used herein, may be defined as a measurement taken in a borehole intersecting an earth formation indicative of a parameter of interest of the borehole, the formation, or a fluid therein, i.e., a downhole parameter. Aspects of the present disclosure relate to fluid analysis. Techniques described herein are particularly suited to measurement of values of properties of a downhole fluid through the use of instruments utilizing sonoluminescence phenomena. These values may be used to evaluate and model the formation or the borehole, and for conducting further operations in the formation or the borehole.

The present disclosure is susceptible to embodiments of different forms. There are shown in the drawings, and herein will be described in detail, specific embodiments of the present disclosure with the understanding that the present disclosure is to be considered an exemplification of the principles of the disclosure, and is not intended to limit the disclosure to that illustrated and described herein. Indeed, as will become apparent, the teachings of the present disclosure can be utilized for a variety of well tools and in all phases of well construction and production. Accordingly, the embodiments discussed below are merely illustrative of the applications of the present disclosure.

Figure 2:
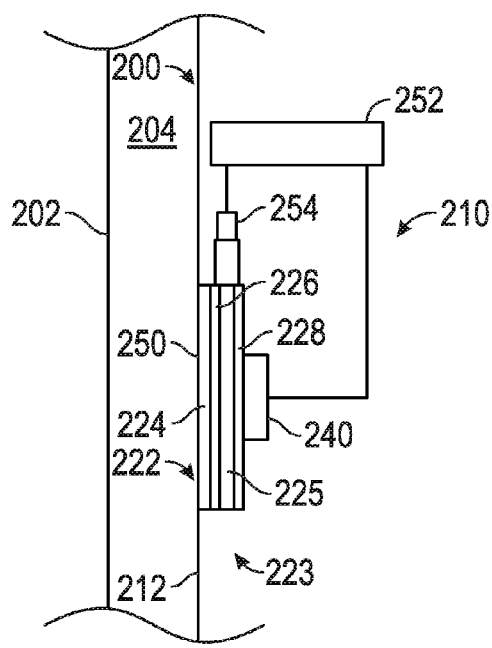
FIG. 2 illustrates a tool including at least one sonoluminescence measurement instrument in accordance with embodiments of the invention.

FIG. 2 illustrates a tool including at least one sonoluminescence measurement instrument in accordance with embodiments of the invention. Referring to FIG. 2, tool 200 includes at least one sonoluminescence instrument and is configured to be conveyed in a borehole 202. A sonoluminescence measurement instrument 210 configured to measure a parameter of interest is mounted on the tool 200. In some embodiments, the sonoluminescence instrument 210 may include a surface in contact with the borehole fluid, and some (or all) of sonoluminescence instrument 210 may protrude from the tool body 212 into the borehole 202. In other embodiments, the tool 200 may include a fluid testing assembly configured to extract downhole fluid from the borehole and deliver the fluid to the sonoluminescence measurement instrument 210 for testing. The fluid testing assembly may include a sample chamber which may be filled and emptied via the use of various valves, or may operate using a continuous flow line.

In one example, instrument 210 comprises an optically transparent piezoelectric transducer assembly 220 comprising an acoustic matching plate 224 backed by a transducer 223 comprising a substantially transparent piezoelectric ceramic material 225 such as lithium niobate, or lead lanthanum zirconate titanate from Ecertec Ltd., Leeds, United Kingdom or for operation at lower temperatures, polymers such as polyvinylidene difluoride (PVDF) or alternate layers of poly-L-lactic acid (PLLA) and optical isomer poly-D-lactic acid (PDLA) or for if less abrasion resistance is permissible, two-dimensional piezoelectric structures of graphene or molybdenum disulfide (MoS2) whose transparency comes from their extreme thinnesswith transparent indium tin oxide (ITO), tin oxide (TO), cadmium tin oxide, Cd2SnO4, or other transparent conductive electrodes 226, 228 on opposite surfaces. Plate 224 is bonded to the transducer 223 such that they are acoustically coupled. A portion (e.g., face 222) of the transducer assembly 220 may be immersed in the downhole fluid 204, forming an interface 250 between the assembly 220 and the fluid 204. A protective layer made of diamond-like carbon (DLC) based film, such as those doped with boron or silicon (e.g., Si-DLC) or the like, may be employed on the substrate, which can be tuned in electrical and optical properties along with applying the appropriate deposition mechanism.

A detector (e.g., a CCD photodetector) 240 optically coupled to the transducer assembly 220 detects sonoluminescence (e.g., light emissions) traversing the transducer assembly 220. Tool 200 may include circuitry for making measurements using the instrument 210. Circuitry may include control unit 252 operatively connected to transducer assembly 220 and detector 240 and a drive circuit 254 controlled by control unit 252 and electrically connected to electrodes 226 and 228, by which power is supplied to the transducer 223 to produce sonoluminescence. The circuitry may be timed (e.g., electronically gated) to detect the sonoluminescence. Light emissions (flashes) from the bubbles may be extremely short (e.g., between 25 and a few hundred picoseconds long) with peak intensities less than $10^{-9}$ mW.

Controller 252 may be implemented as the at least one processor described above with reference to FIGS. 1A & 1B or may be an additional processor or other supporting circuitry. Controller 252 may be located at the instrument, at other locations in the tool (including, for example, in other subs), or at the surface.

In operation, the instrument may be controlled by control unit 252 (e.g., a processor), which actuates the transducer 223 while the portion 222 is immersed in the downhole fluid to generate cavitation in the fluid 204 sufficient to generate sonoluminescence at the interface 250 and receives measurement information (e.g., data) from detector 240. Detector 240 may be implemented as a spectrometer or other spectrographic detector including a mechanism for separating light into component wavelengths and a detector for sensing the intensity at each wavelength.

In order to operate the downhole tool 200 and/or provide a communications interface with at least one processor at the surface, the downhole tool 210 may include a downhole processor (not shown). In one embodiment, electronics (not shown) associated with the sensors may be configured to record information related to the parameters to be estimated. In some embodiments, the parameter of interest may be estimated using the recorded information.

In other embodiments, such electronics may be located elsewhere (e.g., at the surface). To perform estimation of a parameter during a single trip, the tool may use a "high bandwidth" transmission to transmit the information acquired by sensors to the surface for analysis. For instance, a communication line for transmitting the acquired information may be an optical fiber, a metal conductor, or any other suitable signal conducting medium. It should be appreciated that the use of a "high bandwidth" communication line may allow surface personnel to monitor and control the treatment activity in near real-time.

In some embodiments, processors may include electromechanical and/or electrical circuitry configured to control one or more components of the tool 200. In other embodiments, processors may use algorithms and programming to receive information and control operation of the tool 200. Therefore, processors may include an information processor that is in data communication with a data storage medium and a processor memory. The data storage medium may be any standard computer data storage device, such as a USB drive, memory stick, hard disk, removable RAM, EPROMs, EAROMs, flash memories and optical disks or other commonly used memory storage system known to one of ordinary skill in the art including Internet based storage. The data storage medium may store one or more programs that when executed causes information processor to execute the disclosed method(s). Herein, "information" may include raw data, processed data, analog signals, and digital signals.

A surface control unit and/or downhole control unit may be configured to control sensors described above and to estimate a parameter of interest according to methods described herein. Control of these components may be carried out using one or more models or algorithms using methods described below.

Mathematical models, look-up tables, or other models representing relationships between the signals and the values of the formation properties may be used to characterize operations in the formation or the formation itself, optimize one or more operational parameters of a production or development, and so on. The system may carry out these actions through notifications, advice, and/or intelligent control.

Figure 3:
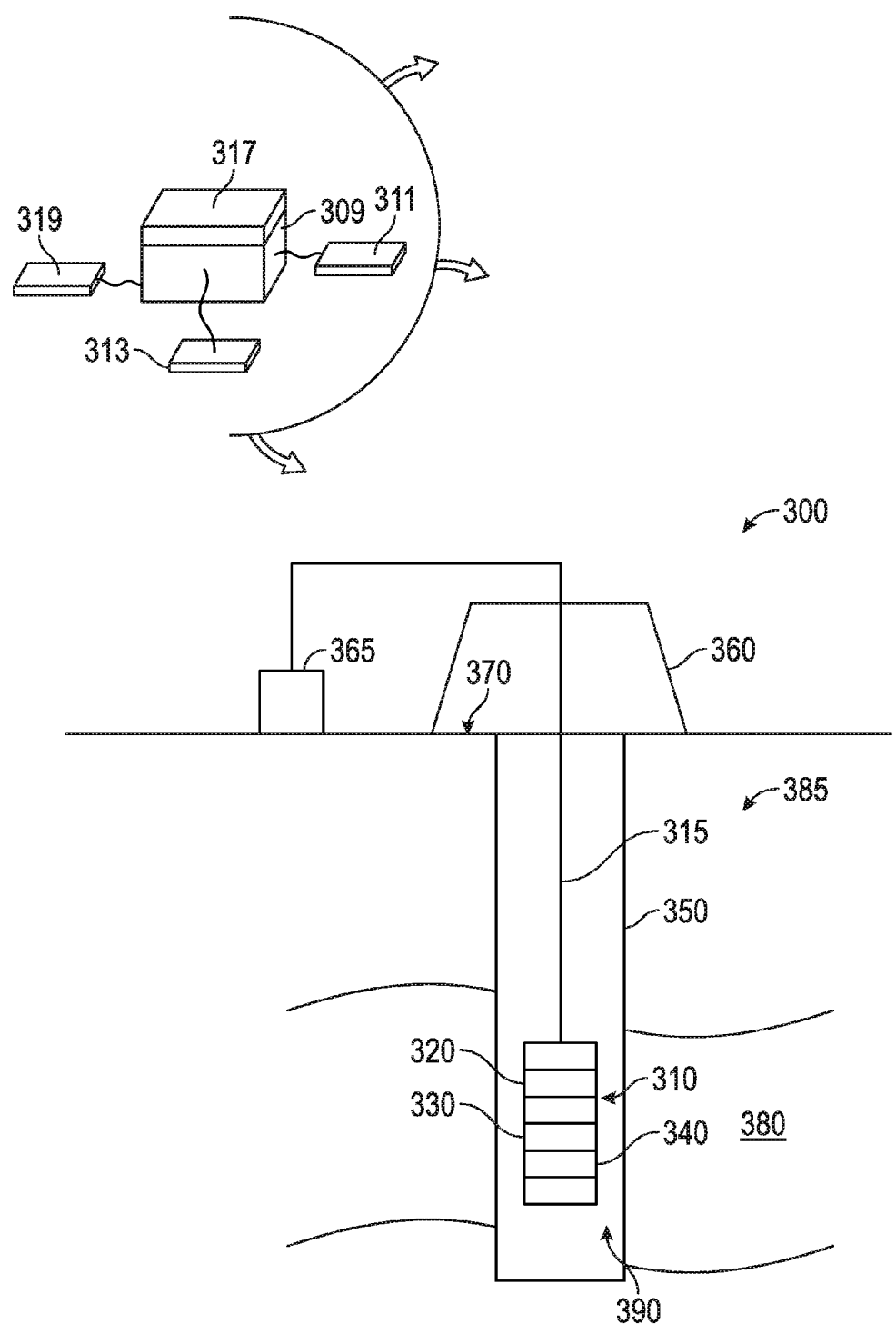
FIG. 3 schematically illustrates a system having a downhole tool configured to acquire information for estimating a downhole parameter of interest using sonoluminescence.

FIG. 3 schematically illustrates a system 300 having a downhole tool 310 configured to acquire information for estimating a downhole parameter of interest (e.g., a value of a property of the formation 380, the borehole 350, or downhole fluid 390 therein) using sonoluminescence instrument 340.

The system 300 may include a conventional derrick 360 erected on a derrick floor 370. A conveyance device (carrier 315) which may be rigid or non-rigid, may be configured to convey the downhole tool 310 into wellbore 350 in proximity to a volume of interest 380 of an earth formation 385. The carrier 315 may be a drill string, coiled tubing, a slickline, an e-line, a wireline, etc. Downhole tool 310 may be coupled or combined with additional tools e.g., some or all the information processing system (inset). Thus, depending on the configuration, the tool 310 may be used during drilling and/or after the wellbore 350 has been formed. As described herein, "borehole" or "wellbore" refers to a single hole that makes up all or part of a drilled well. While a land system is shown, the teachings of the present disclosure may also be utilized in offshore or subsea applications. The carrier 315 may include embedded conductors for power and/or data for providing signal and/or power communication between the surface and downhole equipment (e.g., a seven conductor cable). The carrier 315 may include a bottom hole assembly, which may include a drilling motor for rotating a drill bit.

Downhole fluid (e.g., drilling fluid, or 'mud') 390 may be present between the formation 385 and the downhole tool 310. A surface control system 365 receives signals from instrument(s) 340 or electronics 330 indicative of measurements of the downhole fluid 390 and other sensors used in the system 300 and processes such signals according to programmed instructions provided to the surface control system 365. The surface control system 365 may display desired parameters and other information on a display/monitor that is utilized by an operator. The surface control system 365 may further communicate with a downhole control system 320 at a suitable location on downhole tool 310. The surface control system 365 may process data relating to the operations and data from the instrument 340, and may control one or more downhole operations performed by system 300, including operation of fluid collection system 325.

In one embodiment, electronics 330 associated with instrument 340 may be configured to record and/or process the information obtained. Certain embodiments of the present disclosure may be implemented with a hardware environment that includes an information processor 317, an information storage medium 313, an input device 311, processor memory 309, and may include peripheral information storage medium 319. The hardware environment may be in the well, at the rig, or at a remote location. Moreover, the several components of the hardware environment may be distributed among those locations. The input device 311 may be any data reader or user input device, such as data card reader, keyboard, USB port, etc. The information storage medium 313 stores information provided by the detectors. Information storage medium 313 may include any non-transitory computer-readable medium for standard computer information storage, such as a USB drive, memory stick, hard disk, removable RAM, EPROMs, EAROMs, flash memories and optical disks or other commonly used memory storage system known to one of ordinary skill in the art including Internet based storage. Information storage medium 313 stores a program that when executed causes information processor 317 to execute the disclosed method. Information storage medium 313 may also store the formation information provided by the user, or the formation information may be stored in a peripheral information storage medium 319, which may be any standard computer information storage device, such as a USB drive, memory stick, hard disk, removable RAM, or other commonly used memory storage system known to one of ordinary skill in the art including Internet based storage. Information processor 317 may be any form of computer or mathematical processing hardware, including Internet based hardware. When the program is loaded from information storage medium 313 into processor memory 309 (e.g. computer RAM), the program, when executed, causes information processor 317 to retrieve detector information from either information storage medium 313 or peripheral information storage medium 319 and process the information to estimate a parameter of interest. Information processor 317 may be located on the surface or downhole.

The term "information" as used herein includes any form of information (analog, digital, EM, printed, etc.). As used herein, a processor is any information processing device that transmits, receives, manipulates, converts, calculates, modulates, transposes, carries, stores, or otherwise utilizes information. In several non-limiting aspects of the disclosure, an information processing device includes a computer that executes programmed instructions for performing various methods. These instructions may provide for equipment operation, control, data collection and analysis and other functions in addition to the functions described in this disclosure. The processor may execute instructions stored in computer memory accessible to the processor, or may employ logic implemented as field-programmable gate arrays ('FPGAs'), application-specific integrated circuits ('ASICs'), other combinatorial or sequential logic hardware, and so on.

To perform the treatments during a single trip, the tool may use a high bandwidth transmission to transmit the information acquired by electronics 330 via instrument 340 to the surface for analysis. For instance, a communication line for transmitting the acquired information may be an optical fiber, a metal conductor, or any other suitable signal conducting medium. It should be appreciated that the use of a "high bandwidth" communication line may allow surface personnel to monitor and control operations in "substantially real-time."

One point of novelty of the system illustrated in FIG. 3 is that the surface control system 365 and/or the downhole control system 320 are configured to perform certain methods (discussed below) that are not in the prior art. A surface control system or downhole control system may be configured to control the tool described above and any incorporated sensors and to estimate a parameter of interest according to methods described herein.

Aspects of the present disclosure are subject to application in various different embodiments. In some general embodiments, carrier 315 is implemented as a tool string of a drilling system, and measurements taken in the borehole may be characterized as "logging-while-drilling" (LWD) or "measurement-while-drilling" (MWD) operations.

Figure 4:
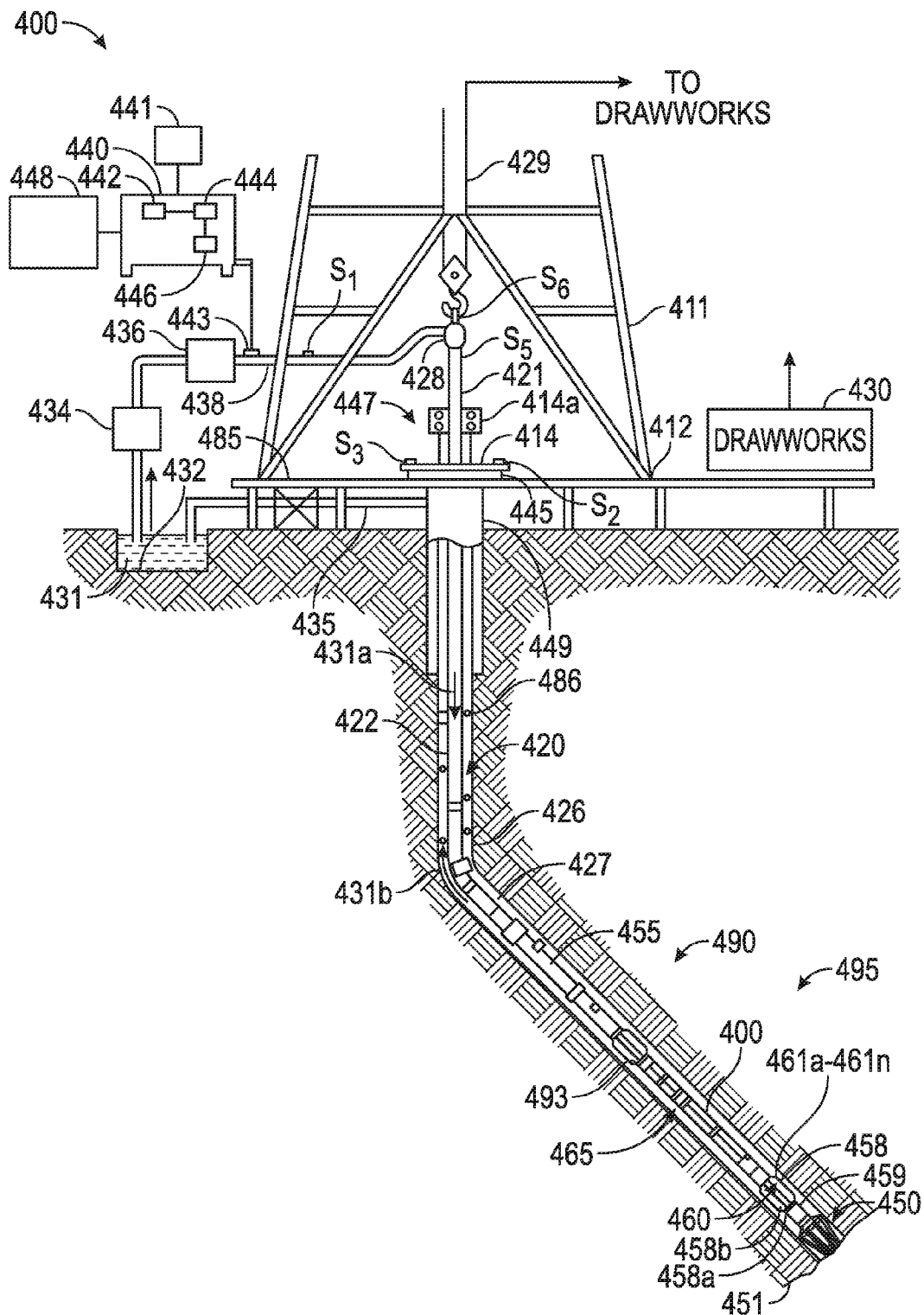
FIG. 4 shows an example embodiment of an MWD system for downhole evaluation using sonoluminescence.

FIG. 4 shows an example embodiment of an MWD system for downhole evaluation using sonoluminescence. The system 401 includes a carrier 411 that is shown disposed in a wellbore or borehole 426 that penetrates at least one earth formation 495. The system 401 also includes a tool 410 configured for conducting sonoluminescence-based fluid analysis in the borehole.

FIG. 4 shows a drill string 420 including a bottomhole assembly (BHA) 490 conveyed in the borehole 426 as the carrier. The drilling system 401 includes a conventional derrick 411 erected on a platform or floor 412 which supports a rotary table 414 that is rotated by a prime mover, such as an electric motor (not shown), at a desired rotational speed. A tubing (such as jointed drill pipe 422), having the drilling assembly 490, attached at its bottom end extends from the surface to the bottom 451 of the borehole 426. A drill bit 450, attached to drilling assembly 490, disintegrates the geological formations when it is rotated to drill the borehole 426. The drill string 420 is coupled to a drawworks 430 via a Kelly joint 421, swivel 428 and line 429 through a pulley. Drawworks 430 is operated to control the weight on bit ("WOB"). The drill string 420 may be rotated by a top drive (not shown) instead of by the prime mover and the rotary table 414. Alternatively, a coiled-tubing may be used as the tubing 422. A tubing injector 414a may be used to convey the coiled-tubing having the drilling assembly attached to its bottom end. The operations of the drawworks 430 and the tubing injector 414a are known in the art and are thus not described in detail herein.

It should be understood that embodiments of the present disclosure are well suited for use in wells having various configurations including horizontal wells, deviated wells, slanted wells, multilateral wells and so on. Accordingly, use of directional terms herein (e.g., above, below, upper, lower, upward, downward, topmost, lowermost, uphole, downhole, etc) refer to the direction of travel along the borehole either toward or away from the surface, with the upward direction being toward the surface and the downward direction being away from the surface.

A suitable drilling fluid 431 (also referred to as the "mud") from a source 432 thereof, such as a mud pit, is circulated under pressure through the drill string 420 by a mud pump 434. The drilling fluid 431 passes from the mud pump 434 into the drill string 420 via a discharger 436 and the fluid line 438. The drilling fluid 431a from the drilling tubular discharges at the borehole bottom 451 through openings in the drill bit 450. The returning drilling fluid 431b circulates uphole through the annular space 427 between the drill string 420 and the borehole 426 and returns to the mud pit 432 via a return line 435 and drill cutting screen 485 that removes the drill cuttings 486 from the returning drilling fluid 431b. A sensor S1 in line 438 provides information about the fluid flow rate. A surface torque sensor S2 and a sensor S3 associated with the drill string 420 respectively provide information about the torque and the rotational speed of the drill string 420. Tubing injection speed is determined from the sensor S5, while the sensor S6 provides the hook load of the drill string 420.

Well control system 447 is placed at the top end of the borehole 426. The well control system 447 includes a surface blow-out-preventer (BOP) stack 415 and a surface choke 449 in communication with a wellbore annulus 427. The surface choke 449 can control the flow of fluid out of the borehole 426 to provide a back pressure as needed to control the well.

In some applications, the drill bit 450 is rotated by only rotating the drill pipe 422. However, in many other applications, a downhole motor 455 (mud motor) disposed in the BHA 490 also rotates the drill bit 450. The rate of penetration (ROP) for a given BHA largely depends on the WOB or the thrust force on the drill bit 450 and its rotational speed.

A surface control unit or controller 440 receives signals from the downhole sensors and devices via a sensor 443 placed in the fluid line 438 and signals from sensors S1-S6 and other sensors used in the system 401 and processes such signals according to programmed instructions provided to the surface control unit 440. The surface control unit 440 displays drilling parameters and other parameters of interest related to the borehole, formation, and drilling operations, and other information on a display/monitor 441 that is utilized by an operator to control the drilling operations. The surface control unit 440 may be a computer-based unit that may include a processor 442 (such as a microprocessor), a storage device 444, such as a solid-state memory, tape or hard disc, and one or more computer programs 446 in the storage device 444 that are accessible to the processor 442 for executing instructions contained in such programs. The surface control unit 440 may further communicate with a remote control unit 448. The surface control unit 440 may process data relating to the drilling operations, data from the sensors and devices on the surface, and data received from downhole; and may control one or more operations of the downhole and surface devices. The data may be transmitted in analog or digital form.

The BHA 490 may include a tool 410 configured for performing sonoluminescence-based fluid analysis downhole. The BHA 490 may also contain other formation evaluation sensors or devices (also referred to as measurement-while-drilling ("MWD") or logging-while-drilling ("LWD") sensors) determining resistivity, density, porosity, permeability, acoustic properties, nuclear-magnetic resonance properties, formation pressures, properties or characteristics of the fluids downhole and other desired properties of the formation 495 surrounding the BHA 450. For convenience, all such sensors are generally denoted herein by numeral 465. The BHA 490 may further include a variety of other sensors and devices 459 for determining one or more properties of the BHA 490, such as vibration, bending moment, acceleration, oscillations, whirl, stick-slip, weight-on-bit, fluid flow rate, pressure, temperature, rate of penetration, azimuth, tool face, drill bit rotation, etc.

The BHA 490 may include a steering apparatus or tool 458 for steering the drill bit 450 along a desired drilling path. In one aspect, the steering apparatus may include a steering unit 460, having a number of force application members 461a-461n. The force application members may be mounted directly on the drill string, or they may be at least partially integrated into the drilling motor. In another aspect, the force application members may be mounted on a sleeve, which is rotatable about the center axis of the drill string. The force application members may be activated using electro-mechanical, electro-hydraulic or mud-hydraulic actuators. In yet another embodiment the steering apparatus may include a steering unit 458 having a bent sub and a first steering device 458a to orient the bent sub in the wellbore and the second steering device 458*b* to maintain the bent sub along a selected drilling direction. The steering unit 458, 460 may include near-bit inclinometers and magnetometers.

The drilling system 401 may include sensors, circuitry and processing software and algorithms for providing information about desired drilling parameters relating to the BHA, drill string, the drill bit and downhole equipment such as a drilling motor, steering unit, thrusters, etc. Many current drilling systems, especially for drilling highly deviated and horizontal wellbores, utilize coiled-tubing for conveying the drilling assembly downhole. In such applications a thruster may be deployed in the drill string 420 to provide the required force on the drill bit.

Example sensors for determining drilling parameters include, but are not limited to drill bit sensors, an RPM sensor, a weight on bit sensor, sensors for measuring mud motor parameters (e.g., mud motor stator temperature, differential pressure across a mud motor, and fluid flow rate through a mud motor), and sensors for measuring acceleration, vibration, whirl, radial displacement, stick-slip, torque, shock, vibration, strain, stress, bending moment, bit bounce, axial thrust, friction, backward rotation, BHA buckling, and radial thrust. Sensors distributed along the drill string can measure physical quantities such as drill string acceleration and strain, internal pressures in the drill string bore, external pressure in the annulus, vibration, temperature, electrical and magnetic field intensities inside the drill string, bore of the drill string, etc. Suitable systems for making dynamic downhole measurements include COPILOT, a downhole measurement system, manufactured by BAKER HUGHES INCORPORATED.

The drilling system 401 can include one or more downhole processors at a suitable location such as 493 on the BHA 490. The processor(s) can be a microprocessor that uses a computer program implemented on a suitable non-transitory computer-readable medium that enables the processor to perform the control of system 401 and processing of information, such as information from the sensors. The non-transitory computer-readable medium may include one or more ROMs, EPROMs, EAROMs, EEPROMs, flash memories, RAMs, hard drives and/or optical disks. Other equipment such as power and data buses, power supplies, and the like will be apparent to one skilled in the art. In one embodiment, the MWD system utilizes mud pulse telemetry to communicate data from a downhole location to the surface while drilling operations take place. The surface processor 442 can process at the surface measured data, along with the data transmitted from the downhole processor, to evaluate the formation.

Surface processor 442 or downhole processor 493 may also be configured to control steering apparatus 458, mud pump 434, drawworks 430, rotary table 414, downhole motor 455, other components of the BHA 490, or other components of the drilling system 401. Surface processor 442 or downhole processor 493 may be configured to control sonoluminescence-based fluid analysis instruments as described above and to estimate a parameter of interest according to methods described herein.

Control of these components may be carried out using one or more models using methods described below. For example, surface processor 442 or downhole processor 493 may be configured to modify drilling operations i) autonomously upon triggering conditions, ii) in response to operator commands, or iii) combinations of these. Such modifications may include changing drilling parameters, steering the drillbit (e.g., geosteering), altering the drilling fluid program, activating well control measures, and so on. Control of these devices, and of the various processes of the drilling system generally, may be carried out in a completely automated fashion or through interaction with personnel via notifications, graphical representations, user interfaces and the like. Reference information accessible to the processor may also be used. In some general embodiments, surface processor 442, downhole processor 493, or other processors (e.g. remote processors) may be configured to operate the sonoluminescence-based fluid analysis tool.

The system 401 may include any number of downhole tools for various processes including formation drilling, geosteering, and formation evaluation (FE) for making electrical measurements versus depth and/or time of one or more physical properties in or around a borehole, including a volume of interest of the formation intersected by the borehole.

Mathematical models, look-up tables, or other models representing relationships between the signals and the parameter values may be used to characterize the borehole, downhole fluid, operations in the formation or the formation itself, optimize one or more operational parameters of a production or development, and so on. The system may carry out these actions through notifications, advice, and/or intelligent control. Various types of downhole parameters may be determined using measurements in accordance with the present disclosure and making evaluations in accordance with embodiments disclosed herein.

Figure 5:
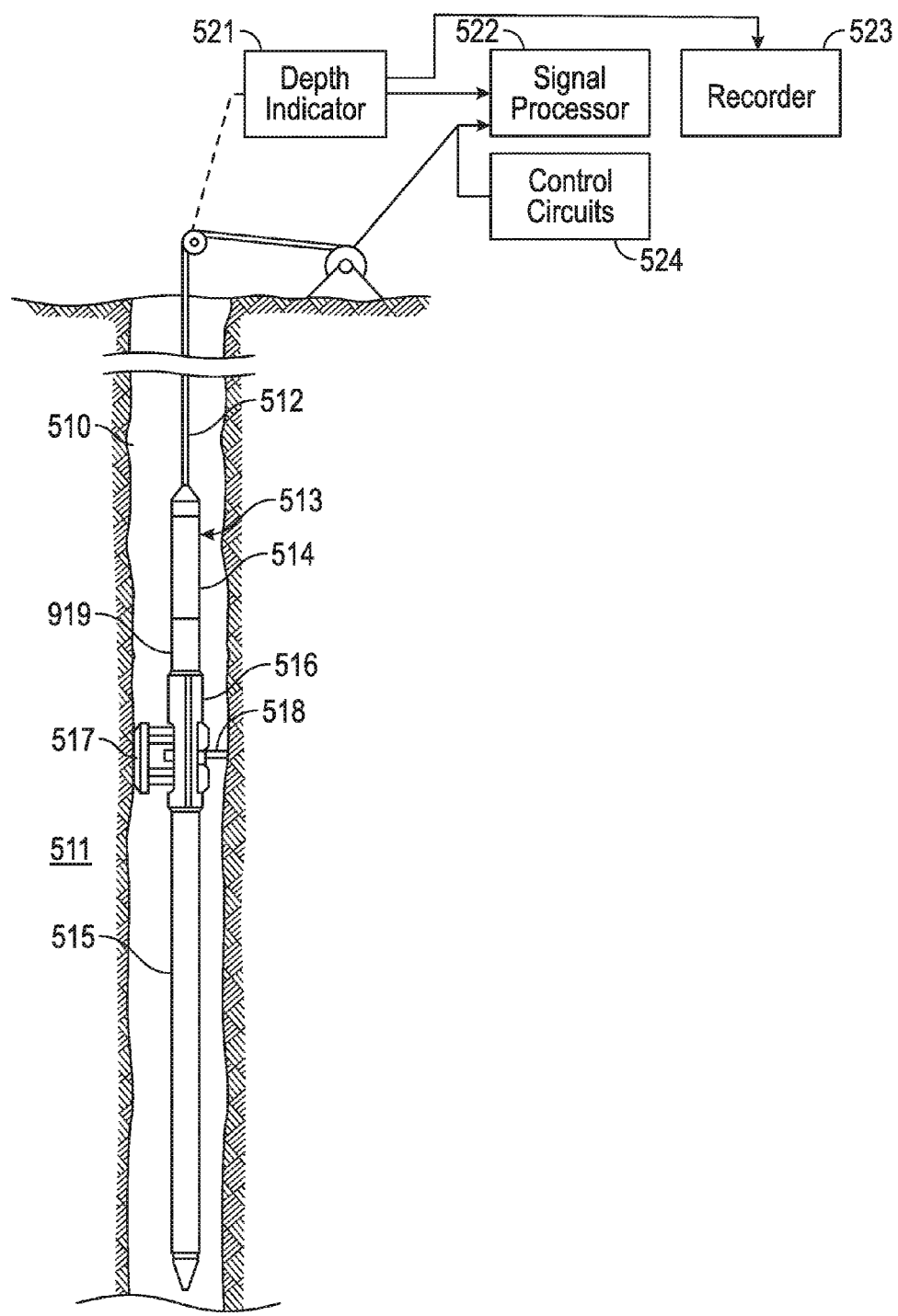
FIG. 5 illustrates a wireline tool in accordance with embodiments of the present disclosure in communication with the formation.

FIG. 5 illustrates a wireline tool in accordance with embodiments of the present disclosure in communication with the formation. Borehole 510 intersects a portion of the earth formation 511. Disposed within the borehole 510 by means of a carrier 512 is a sampling and measuring tool 513 including a sonoluminescence instrument as described above. Carrier 512 may be a drill string, coiled tubing, a slickline, an e-line, a wireline, etc. The sampling and measuring instrument includes hydraulic power system 519, a fluid sample storage section 515 and a sampling mechanism section 516. Sampling mechanism section 516 includes selectively extensible well engaging pad member 517, a selectively extensible fluid admitting sampling probe member 518 and bi-directional pumping member 519. Specific configuration of the components with respect to one another may vary.

In operation, sampling and measuring instrument 513 is positioned within borehole 510 via carrier 512 (e.g., by winding or unwinding cable 512 from a hoist (not shown)). Depth information from a depth indicator 521 is coupled to signal processor 522 and recorder 523 when tool 513 is disposed adjacent an earth formation of interest. Control signals from control circuitry 529 are transmitted through electrical conductors contained within conveyance device 512 to tool 513. Any or all of signal processor 522, control circuitry 529 and recorder 523 may be implemented with one more processors.

Electrical control signals activate an operational hydraulic pump within the hydraulic power system 519 shown, which provides hydraulic power causing the well engaging pad member 517 and the fluid admitting member 518 to move laterally from tool 513 into engagement with the earth formation 511 and the bi-directional pumping member 519. Fluid admitting member or sampling probe 518 can then be placed in fluid communication with the earth formation 511, such as, for example, via electrical control signals from control circuits 529 selectively activating solenoid valves within tool 513 for the taking of a sample of connate fluids contained in the earth formation of interest, or via other actuation techniques. Other collection systems may be used in other embodiments, such as, for example, a system for continuously sampling borehole fluid.

Figure 6:
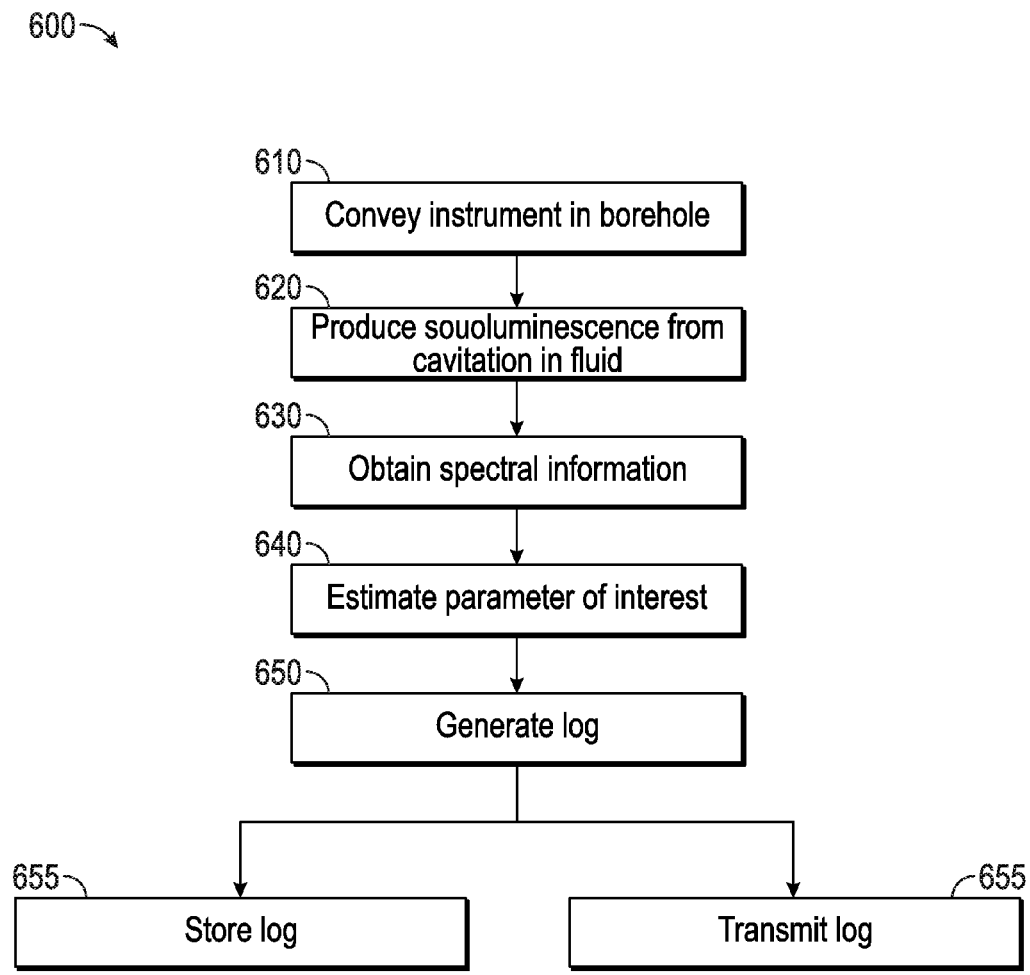
FIG. 6 shows a flow chart illustrating methods for estimating at least one parameter of an earth formation according to one embodiment of the present disclosure.

FIG. 6 shows a flow chart 600 illustrating methods for estimating at least one downhole parameter of interest in accordance with embodiments of the present disclosure. In optional step 610, a sonoluminescence fluid analysis instrument is conveyed in a borehole using a carrier. The borehole is filled with downhole fluid which may be non-transparent.

Step 620 includes using an ultrasonic irradiation device (e.g., a transducer) to produce sonoluminescence from cavitation in a volume of the fluid. The sonoluminescence comprises light emissions over a spectrum of wavelengths, and the spectral information is reflective of the spectrum of wavelengths. Step 620 may include using an optically transparent ultrasonic transducer to produce the cavitation at the interface of the transducer.

Step 630 comprises obtaining spectral information from measurement of the sonoluminescence with a light-responsive device. Step 630 may be carried out by sensing the light emissions from at least one cavitation bubble by a CCD based spectrometer. In some implementations, the light may be filtered by an intervening optical media. The optically transparent transducer may be between the interface and the light-responsive device.

Step 640 comprises estimating a parameter of interest of the fluid from the spectral information. The estimation may be performed in multiple stages, such that an earlier stage may process the information for a later stage.

Step 640 may include using spectral lines to determine the elemental or molecular composition or the corresponding respective concentrations in the sample. Step 640 may be carried out by deconvolving a response spectrum embodied by the spectral information into a plurality of elemental or molecular spectral yields. Methods may include deconvolving the response spectrum using one or more separately determined elemental standard spectra. The spectral information may be expressed as an energy spectrum (the "response spectrum"). See FIG. 1B.

The term "response spectrum" refers to not only the response spectrum as originally acquired, but also after filtering, corrections, or pre-processing is applied. Since the response spectrum may include spectrum components from multiple components (e.g., ions) of excited atoms and molecules, the information may be separated to identify the energy spectrum components contained with the energy spectrum. Standards may be configured to span the expected range of concentrations and compositions of the fluid and may be measured under the same conditions. Together, the known data (the composition of each standard) and the measured data from the instrument form a training set. A relationship may be ascertained between concentrations of the components of interest and the data from the light responsive device. Equations may be determined describing the relationships between these two sets of information. The exact equation or set of equations that make up the calibration may be referred to as a model. The separate energy spectrum components may thus be used for estimating the concentration of at least one component within the cavitation bubble using the model. Deconvolution may include compensating for effects from interactions of the emissions with intervening matter. Deconvolution according to the present disclosure may determine the weighting coefficients resulting in the best fit of the composite to the response spectrum. MBSL spectra show an underlying smooth, slowly-varying continuum due to thermal black body radiation underlying a combination of atomic and molecular spectra.

Spectral lines may be included for each element of interest, or for each element producing significant emissions. Each reference spectrum represents a response curve corresponding to intensity of the emissions across a band of wavelengths. A library of such spectra is available from the National Institute of Standards and Technology's (NIST) Atomic Spectra Database at www.nist.gov, and each element's spectrum constitutes a unique identifying "fingerprint" for that element. For multicomponent spectra, quantification of each element can be done by any of a number of chemometric or other techniques. With a classical least squares (e.g., K-matrix) approach, the best weighted combination of available known spectra (that is, the weighted combination providing the closest fit to the observed mixture spectrum) is identified. With inverse methods, one starts with a training set of mixture spectra for which the composition of each mixture is known, and then applies multiple linear regression, principal components regression, and/or partial least squares regression. Training a neural network to create a model that will predict the composition of an unknown is another alternative.

In other examples, a chemical kinetics model may be employed. As the bubble temperature increases, the reaction system evolves and radicals start to form from molecules in the bubble by thermal dissociation or other mechanisms. Elementary reversible chemical reactions involving species derivable from the component may be modeled, such as, for example, modeling the production rate of each species as a summation of the rate of the variables for all reactions involving that species. See S. Merouani et al. Theoretical estimation of the temperature and pressure within collapsing acoustical bubbles. *Ultrasonics Sonochemistry* 21 (2014), p. 53-59. However, some thermally induced chemical reactions are irreversible in which case the molecular spectra observed may be those of molecular decomposition and/or reassembly fragments rather than the molecular spectra of the original compounds in the fluid.

Optional methods may include using the parameter of interest to estimate a characteristic of a formation associated with the fluid, such as, for example, reservoir compartmentalization. That is, if fluid in one section of a reservoir has a different elemental composition than does fluid in another part of the reservoir, it is likely that there is no fluid communication between those two parts (a fault or some other permeability barrier separates them) else they would have reached a common elemental composition equilibrium. This information can be quite useful when trying to produce a reservoir because unconnected pieces of a reservoir will require separate wells to drain, with all of the expense and effort which that entails. Estimation of the parameter may include the use of a model. In some embodiments, the model may include, but is not limited to, one or more of: (i) a mathematical equation, (ii) an algorithm, (iii) an deconvolution technique, and so on. Reference information accessible to the processor may also be used.

The elemental analysis is useful to determine the origin of fluids in exploration, production, drilling and delivery operations. Fluids from different wells or fluids from different depths in the same well can be compared to determine compartmentalization of the reservoir. In production, changes in elemental composition of a particular zone over time may indicate that drainage of an oil field has started to extent to a new region of the reservoir, and may provide reservoir connectivity information.

Step 650 comprises generating a log of the spectral information. Optional steps 655 comprise performing at least one of: i) storing the log on a on a non-transitory machine-readable medium; and ii) transmitting the log to another processor. Herein, "information" may include raw data, processed data, analog signals, and digital signals.

Estimated parameters of interest may be stored (recorded) as information or visually depicted on a display. The parameters of interest (or other formation resistivity measurement information) may be transmitted before or after storage or display. For example, information may be transmitted to other downhole components or to the surface for storage, display, or further processing. Aspects of the present disclosure relate to modeling a volume of an earth formation using the estimated parameter of interest, such as, for example, by associating estimated parameter values with portions of the volume of interest to which they correspond. The model of the earth formation generated and maintained in aspects of the disclosure may be implemented as a representation of the earth formation stored as information. The information (e.g., data) may also be transmitted, stored on a non-transitory machine-readable medium, and/or rendered (e.g., visually depicted) on a display.

The processing of the measurements by a processor may occur at the tool, the surface, or at a remote location. The data acquisition may be controlled at least in part by the electronics. Implicit in the control and processing of the data is the use of a computer program on a suitable non-transitory machine readable medium that enables the processors to perform the control and processing. The non-transitory machine readable medium may include ROMs, EPROMs, EEPROMs, flash memories and optical disks. The term processor is intended to include devices such as a field programmable gate array (FPGA).

The term "conveyance device" as used above means any device, device component, combination of devices, media and/or member that may be used to convey, house, support or otherwise facilitate the use of another device, device component, combination of devices, media and/or member. Exemplary non-limiting conveyance devices include drill strings of the coiled tube type, of the jointed pipe type and any combination or portion thereof. Other conveyance device examples include casing pipes, wirelines, wire line sondes, slickline sondes, drop shots, downhole subs, BHA's, drill string inserts, modules, internal housings and substrate portions thereof, self-propelled tractors. As used above, the term "sub" refers to any structure that is configured to partially enclose, completely enclose, house, or support a device. The term "information" as used above includes any form of information (Analog, digital, EM, printed, etc.). The term "processor" or "information processing device" herein includes, but is not limited to, any device that transmits, receives, manipulates, converts, calculates, modulates, transposes, carries, stores or otherwise utilizes information. An information processing device may include a microprocessor, resident memory, and peripherals for executing programmed instructions. The processor may execute instructions stored in computer memory accessible to the processor, or may employ logic implemented as field-programmable gate arrays ('FPGAs'), application-specific integrated circuits ('ASICs'), other combinatorial or sequential logic hardware, and so on. Thus, configuration of the processor may include operative connection with resident memory and peripherals for executing programmed instructions.

Method embodiments may include conducting further operations in the earth formation in dependence upon the formation resistivity information, the logs, estimated parameters, or upon models created using ones of these. Further operations may include at least one of: i) extending the borehole; ii) drilling additional boreholes in the formation; iii) performing additional measurements on the formation; iv) estimating additional parameters of the formation; v) installing equipment in the borehole; vi) evaluating the formation; vii) optimizing present or future development in the formation or in a similar formation; viii) optimizing present or future exploration in the formation or in a similar formation; ix) evaluating the formation; and x) producing one or more hydrocarbons from the formation.

While the foregoing disclosure is directed to the one mode embodiments of the disclosure, various modifications will be apparent to those skilled in the art. It is intended that all variations be embraced by the foregoing disclosure.

What is claimed is:

1. A method of evaluating a downhole fluid, the method comprising:
   using ultrasonic irradiation to produce sonoluminescence from cavitation in a volume of a downhole fluid in a borehole intersecting an earth formation;
   obtaining spectral information from measurement of the sonoluminescence with a light-responsive device; and
   estimating a parameter of interest of the fluid from the spectral information.

2. The method of claim 1, wherein the parameter of interest comprises a composition of the fluid.

3. The method of claim 1, wherein the parameter of interest is the concentration of at least one of: i) at least one chemical element in the volume; ii) at least one molecular element in the volume.

4. The method of claim 3, comprising deconvolving a response spectrum represented by the spectral information by using one or more separately determined standard spectra.

5. The method of claim 1, comprising estimating the parameter of interest using spectral lines represented by the spectral information.

6. The method of claim 1, comprising using an optically transparent ultrasonic transducer to produce the cavitation at the interface of the transducer; wherein the optically transparent ultrasonic transducer is disposed between the interface and the light-responsive device.

7. The method of claim 6, wherein the optically transparent ultrasonic transducer serves as an optical window for the sonoluminescence to reach the light-responsive device.

8. The method of claim 1, wherein obtaining spectral information comprises collecting the light emissions from at least one cavitation bubble by an optical sensor.

9. The method of claim 1, wherein the sonoluminescence comprises light emissions over a spectrum of wavelengths, and the spectral information is reflective of the spectrum of wavelengths.

10. The method of claim 1, further comprising using the parameter of interest to estimate a characteristic of a formation associated with the fluid.

11. The method of claim 10, wherein the characteristic is compartmentalization.

12. An apparatus for fluid analysis in a borehole intersecting an earth formation, the apparatus comprising:
   a carrier configured for conveyance in the borehole;
   an ultrasonic irradiation device disposed on the carrier, the device configured to be acoustically coupled with a fluid filling the borehole and configured to produce sonoluminescence from cavitation in a volume of the fluid;
   a light-responsive device optically coupled with the fluid and configured to obtain spectral information from measurement of the sonoluminescence; and at least one processor configured to estimate a parameter of interest of the fluid from the spectral information.

13. The apparatus of claim 12, comprising a conveyance device configured to convey the ultrasonic transducer and the light-responsive device in the borehole.

14. The apparatus of claim 12, wherein the ultrasonic irradiation device comprises an optically transparent ultrasonic transducer configured to produce cavitation in the fluid at the interface of the transducer and the fluid; and wherein the optically transparent ultrasonic transducer is disposed between the interface and the light-responsive device.

\* \* \* \* \*